United States Patent [19]

Marinkovich

[11] 4,031,197

[45] * June 21, 1977

[54] IN VITRO METHOD FOR DETERMINING ALLERGIC HYPERSENSITIVITY

[75] Inventor: Vincent A. Marinkovich, Palo Alto, Calif.

[73] Assignee: GTE New Ventures Corporation, Stamford, Conn.

[ * ] Notice: The portion of the term of this patent subsequent to Mar. 2, 1993, has been disclaimed.

[22] Filed: July 7, 1975

[21] Appl. No.: 593,649

Related U.S. Application Data

[63] Continuation-in-part of Ser. No. 354,881, April 25, 1973, Pat. No. 3,941,876.

[52] U.S. Cl. ............................. 424/1; 23/230 B; 23/253 TP; 252/408; 424/8; 424/12; 424/91
[51] Int. Cl.$^2$ ................ G01N 33/00; A61B 10/00
[58] Field of Search .................. 424/1, 8, 12, 91; 23/230 B, 253 TP; 252/408

[56] References Cited

UNITED STATES PATENTS

| 3,443,903 | 5/1969 | Haack | 23/230 B |
| 3,549,328 | 12/1970 | Kilburn | 23/230 B |
| 3,838,012 | 9/1974 | Higgins | 23/230 B |

OTHER PUBLICATIONS

Immunochemistry, vol. 4, pp. 11–22 (1967).
The Journal of Immunology, vol. 99, pp. 849–858.
Int. Rev. Cytol., vol. 5, p. 1 (1956).
Nature, vol. 194, p. 495 (1962).

Primary Examiner—Benjamin R. Padgett
Assistant Examiner—Christine M. Nucker

[57] ABSTRACT

Allergic hypersensitivity of a number of patients to a large number of allergens is determined by coating a sheet of cellulosic material on both sides with an adherent hydrophobic material so as to leave a plurality of uncoated islands on one side of the sheet which are in register with a plurality of uncoated islands on the other side of the sheet and with the islands so placed that they lie in horizontal and vertical rows on the sheet, contacting each vertical row of islands with a separate identified allergen, contacting each horizontal row of islands with the serum of a patient, contacting all of the islands with an anti-IgE specific antiserum labeled with either a fluorescent material or a radioactive material and then identifying the islands containing fluorescent or radioactive material. Apparatus for carrying out the determination is described.

6 Claims, 10 Drawing Figures

U.S. Patent    June 21, 1977    Sheet 1 of 2    4,031,197
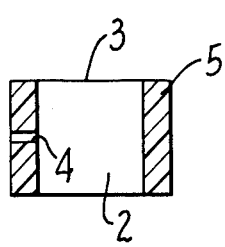
FIG. 2.
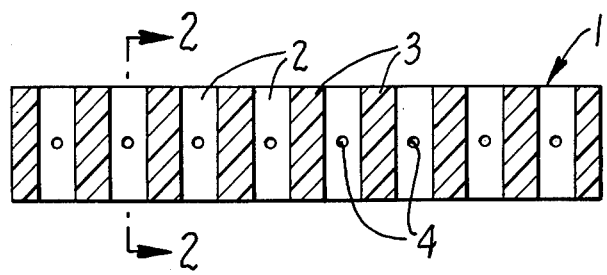
FIG. 1.
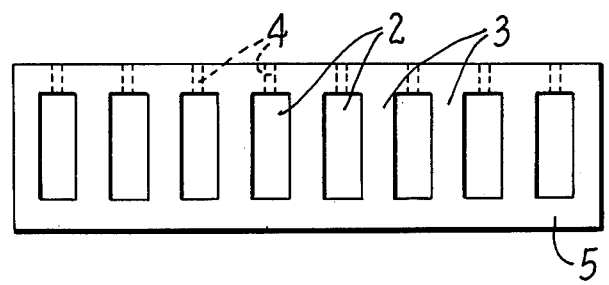
FIG. 3.
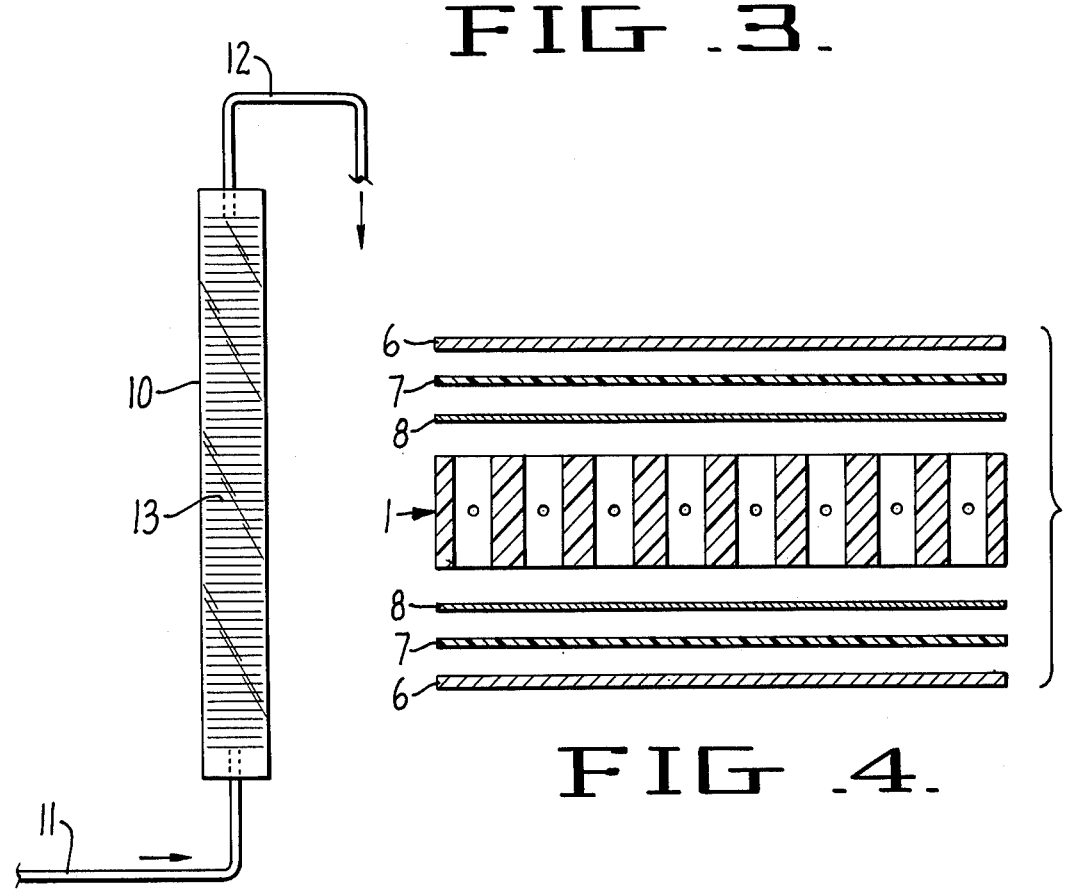
FIG. 4.
FIG. 5.

IN VITRO METHOD FOR DETERMINING ALLERGIC HYPERSENSITIVITY

This application is a continuation-in-part of my copending application Ser. No. 354,881 filed Apr. 25, 1973, now U.S. Pat. No. 3,941,876.

BACKGROUND OF THE INVENTION

Approximately ten percent of all human beings can be designated allergic or atopic. They have become sufficiently hypersensitive to substances commonly present in the environment to experience significant symptoms of exposure to these substances. The majority suffer from readily identifiable allergic symptoms such as hayfever, asthma, eczema, hives and localized swellings. Regardless of symptoms, the preferred methods of therapy are either to remove the patient from the substance to which he is sensitive or, failing that, to treat the patient with increasing doses of the substance and thereby elevate his threshold for reaction. The allergic symptoms are induced by the presence of allergens in the substances to which the individuals are sensitive. An allergen may be defined by first defining an antigen which is a substance that can stimulate the production of antibody in an animal, the produced antibody is specifically reactive with the antigen. An allergen is a special antigen which stimulates a synthesis of a class of antibody which causes allergy. Before either of the methods of therapy noted above can be applied, it is necessary to identify the allergen. Currently, allergic hypersensitivity is determined by direct skin tests on patients. In the skin tests minute quantities of various allergens are injected into or under the skin, visible but usually readily tolerated lesions will appear on the skin of the patient at the point of injection of an allergen to which the patient is hypersensitive. The skin test has limitations. It does not work well in either the very young or the very old, there is some risk to the patient during skin testing and there are relatively few physicians expert in performing and interpreting skin tests so that this method cannot be made widely available and the method is a costly one. An in vitro system for assaying allergic hypersensitivity would be simpler, safer and cheaper than the skin test method. Such a system has not heretofore been available.

BRIEF SUMMARY OF THE INVENTION

Pursuant to the present invention hypersensitivity to a large number of allergens is determined in vitro by testing a small sample of the blood serum of the patient. Briefly, the method consists in bonding a plurality of separate allergens to an elongated porous support body to form a series of narrow bands of bonded allergen separated by narrow bands of allergen-free support, then contacting the allergen bonded support with blood serum of the patient, then contacting the support with anti-immunoglobulin E specific antiserum labeled with either a fluorescent material or with a radioactive material, washing the support to remove unreacted immunoglobulin E anitserum and then identifying those bands containing the fluorescent or radioactive material. The presence of either fluorescent material or radioactive material on a particular band indicates that the allergen initially placed on that band is an allergen to which the patient is hypersensitive. The method may be varied to permit the testing of sera from a number of patients to determine hypersensitivity to a number of allergens by coating a large cellulosic sheet with a water impervious coating but leaving a plurality of uncoated islands on the sheet. The islands are so arranged that each island lies in a vertical row of islands and also in a horizontal row of islands. Each horizontal row of islands is contacted with a separate allergen with the result that the islands in each vertical row are each impregnated with a different allergen. Each vertical row of islands is then contacted with the serum of a different patient to permit allergen-sera reactions. The sheet is then washed and contacted with labeled anti-immunoglobulin E specific antiserum. The sheet is then washed and read. Each island in a vertical row that shows the presence of the labeling agent indicates hypersensitivity of the patient whose serum contacted that row to the specific allergen with which that specific island is impregnated.

DETAILED DESCRIPTION OF THE INVENTION

The appended drawings illustrate three methods of preparing bodies of cellulosic material having narrow bands of separate identified allergens distributed along the length of the body of material.

FIG. 1 is a cross section of a jig arrangement used to impregnate a strip of cellulosic paper with narrow bands of allergen.

FIG. 2 is a lateral cross section of a jig taken through A—A of FIG. 1.

FIG. 3 is a plan view of the jig device.

FIG. 4 is an expanded longitudinal cross section of the jig arrangement showing the assembly of parts used in impregnating the cellulosic paper with narrow bands of various allergenic materials.

FIG. 5 is a front view of an alternate arrangement for producing a plurality of narrow bands of cellulose impregnated with various allergens in a columnar arrangement.

FIG. 6 is an isometric view of the top and bottom members of a jig arrangement with a multi-island paper shown between them.

FIG. 7 is a vertical cross section of the jig assembled with the multi-island paper held between the top and bottom members of the jig.

FIG. 8 is a fragment of FIG. 7 showing a single island area lying between registering troughs in the top and bottom members of the jig.

FIG. 9 is a plan view of the bottom member of the jig with the multi-island paper overlaying the troughs in the bottom member.

Figure 9:
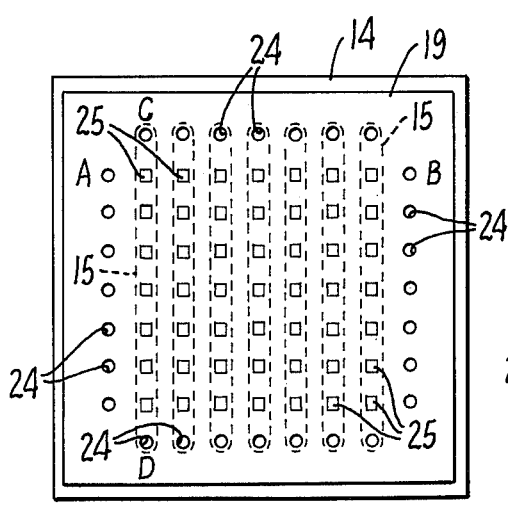
Figure 10:
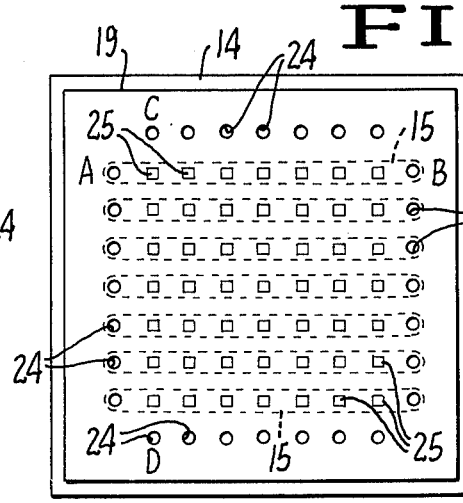

FIG. 10 corresponds to FIG. 9 but shows the multi-island paper and the jig member rotated 90° relative to each other.

Referring now to FIG. 1, the body 1 of the jig may be fabricated from plastic or metal. Reservoirs 2 are open spaces within the body of the jig adapted to receive the allergen solutions. The open reservoirs are separated by solid sections 3 so that along the length of the jig there are series of alternate open and solid sections. Apertures 4 are openings into the reservoirs to permit the introduction of the allergen solutions. The reservoirs 2 are open at top and bottom of the jig. The jig assembly prior to introduction of the allergen solutions is shown in FIG. 4. Strips of paper 8 are laid across top and bottom of jig, over the strips of paper are laid thin sheets of styrofoam or foamed rubber 7 and over the styrofoam or rubber are laid solid metal plates 6. These materials are clamped together so that the paper is held securely across the top of the jig compressed by the porous material 7 and held by steel plates 6. After the assembly is clamped, separate identified allergens are injected into each of the reservoirs through apertures 4 until the reservoirs are completely filled and the allergenic solutions are in contact with the paper at top and bottom of the jig. After the reservoirs are filled, the apertures 4 are closed.

Prior to assembling the jig arrangement shown in FIG. 4, the paper strips 8 are inpregnated with a cyanogen halide.

If desired, a control comparison can be made by filling a few of the reservoirs with a material other than an allergen, i.e., distilled water or a dilute solution of animal protein, the animal being a specie other than the specie from which the serums used in the method are obtained.

FIG. 5 illustrates an alternate arrangement of an elongated cellulosic body in columnar form. Glass or metal column 10 is filled by introducing a thin layer of powdered cellulose impregnated with a cyanogen halide, then a thin layer of unimpregnated cellulose, then a further layer of cyanogen halide impregnated cellulose and so on until the column is filled. Each layer of cyanogen halide impregnated cellulose is contacted with a solution of a specific identified allergen before it is placed in the column. After the column is filled it is sealed. Tube 11 is used for introduction of the several solutions used in the process into the column so that the solutions flow upwardly in the column contacting each of the layers of cellulose and after the column is filled, the solution leaves the column through tube 12 which may be attached to the bottom of a second column, etc. Instead of packing the column with separate layers of allergen containing cellulose and allergen-free cellulose, cellulose containing each of the allergens can be compressed into wafers or sandwiched between two thin sheets of a porous or perforate film (mylar, nylon, etc.) and wafers having diameters approximating the diameter of the column diameter can be cut from the sheets and slid into the column to form a stack of wafers each having a different allergen bonded to the cellulose filling.

The cyanogen halide is used to improve the adherence of the allergen to the cellulose. Other materials such as N,N'-dicyclohexylcarbodiimide may be used for this purpose or the cellulose may simply be kept in contact with the allergen for a longer period of time to obtain adequate adherence to the cellulose without recourse to the aid of any binding agent. FIG. 6 of the appended drawings is an isometric view of a jig used for impregnating island areas on a cellulosic sheet with the liquid used in the practice of the method. The top and bottom members of the jig are separated and the cellulosic sheet is shown between them.

Bottom member 14 of the jig is a flat generally rectangular block made of metal such as stainless steel or of a plastic such as polymethylmethacrylate, polyethyleneterephthalate, polypropylene, nylon or the like. Parallel troughs 15 are cut in the upper surface of the bottom member. Top member 16 of the jig corresponds generally to bottom member 14 in shape and material of construction. Troughs 17 are parallel troughs cut in the lower face of top member 16 and are so spaced that they are in register with troughs 15 of lower member 14 when the jig is assembled. Channels 18 are generally cylindrical passages cut through the body of top member 16 and communicate with the ends of troughs 17. These channels permit introduction of liquid reagents into the jig when it is assembled. Sheet 19 is a sheet of cellulosic material which is coated with a water repellent material so as to leave a plurality of islands 20 which are uncoated on the sheet. The islands are so arranged that they lie in straight rows.

FIG. 7 of the drawing shows the jig assembled with the cellulosic sheet lying between the top and bottom members of the jig. Top member 16 and bottom member 14 are tightly bonded through the use of bolts 21. Other fastening means may be used instead of bolts, it being necessary only that the top and bottom members be held tightly together. Troughs 15 in the lower member and troughs 17 in the upper member are in register with each other and the island areas on sheet 19 are aligned along the trough lengths in the assembly as shown. The assembled jig is held by clamp 22 which is attached to a rocking means 23 which rocks the assembled jig backward and forward to cause sloshing of the reagent in the troughs and so insures good contact with the island areas of sheet 19.

FIG. 8 of the drawings shows the detail of a cross section of the assembled jig showing trough 17 in register with trough 15 and an island area of sheet 19 lying between the two troughs.

FIGS. 9 and 10 show sheet 19 overlaying bottom member 14 in detail.

Sheet 19 is perforated with holes 24 which are so spaced that they lie over the ends of the troughs when the sheet is laid down on bottom member 14. These openings permit reagent to flow through the channels 18 in the upper member of the plate into troughs 17 in the upper member of the plate and through the openings 24 to fill troughs 15 in the lower member of the jig. The island areas 20 on sheet 19 are so spaced that they lie in vertical rows and in horizontal rows. In FIG. 9 the vertical row CD of islands overlays the trough 15 in the bottom member. Similarly, the other vertical rows overlay the other troughs 15 in the bottom member. In FIG. 10 the jig has been rotated 90° relative to sheet 19 so that the horizontal rows AB overlay trough members 15 in the lower member of the jig. In the sheet illustrated in FIGS. 9 and 10, islands 20 are so spaced both horizontally and vertically that either horizontal or vertical rows will be in register with the troughs 15 when the jig is in the position shown in FIG. 9 and again when the jig is in the position shown in FIG. 10. If desired, the spacing between the islands in the vertical rows and horizontal rows need not be the same but only be equal, but in the event that they are not the same, then one jig would be required to impregnate the island areas on the sheet with a first reagent and the second jig having the troughs arranged to accommodate the different spacing would be used to impregnate the island areas with a second reagent.

The several steps of the process using the jig arrangement shown in FIGS. 6–10 are carried out as follows:

A. Islands 20 are preferably impregnated with a material which can assist in bonding an allergen to the sheet, such as a cyanogen halide, for instance, cyanogen bromide.

B. The sheet 19 is laid down on bottom member of the jig 14 so that the vertical rows of islands 20 on the sheet are in register with troughs 15. Top member of the jig 16 is then laid down on the sheet so that troughs 17 are in register with the vertical rows of islands and the jig members are then firmly clamped together. A separate identified allergen solution is then passed through each channel 18 in the top jig member and flows into the troughs of the jig passing through circular openings 24 in the paper in order to reach the troughs of the lower jig member. When each of the troughs has been reasonably filled with a separate identified allergen, channels 18 are closed off by sealing with a strip of adherent plastic 26. The jig is then rotated at room temperature for a time sufficient to insure adequate contact of the allergenic solutions with the island areas on sheet 19. After jig rotation is complete, plastic strips 26 are removed and the residual allergenic solutions are removed from each of the troughs and may be stored for future use. The troughs are then filled with dilute sodium bicarbonate solution or with water and apertures 18 are again sealed with plastic strips 26. The jig is rotated to permit the bicarbonate solution to wash excess allergenic material from the surface of the island areas which have been contacted with it. The bicarbonate solution is removed from the troughs and top member 16 of the jig is lifted from contact with sheet 19.

C. If sheet 19 is to be stored instead of promptly used, it is washed first with buffer A and then with buffer B and then can be stored indefinitely in a body of buffer B at temperatures of −40° C. or below. Buffer A is a 0.1 molar acetate buffer having a pH about 4.0. A 100 cc. lot of buffer A can be prepared by mixing together 41 milliliters of 0.2 molar acetic acid, 9 milliliters of 0.2 molar sodium acetate, and 50 milliliters of distilled water. Buffer B is a phosphate buffered saline solution having a pH about 7.5. About 1 liter of buffer B can be prepared by mixing together 500 milliliters of 0.1 molar phosphate buffer, 500 milliliters of a 0.9 weight percent sodium chloride solution, 10 milliliters of a 5 weight percent sodium azide and 3 grams of human serum albumin.

D. Sheets 19 prepared as above can be used immediately or after long periods of storage as desired. To use a stored sheet, the sheet is first thawed and then laid down on bottom member 14 of the jig being rotated 90 degrees from the position it occupied during impregnation of the island areas with the allergenic solutions. The island areas of sheet 19 are in register with troughs 15 of lower jig members 14 so that the horizontal rows of islands lie along the trough length. Top member 16 of the jig is then laid down on sheet 19 so that its troughs 17 are in register with the horizontal rows of islands. The jig is clamped together and then the blood serum of a particular individual patient is introduced into each channel 18 to fill a trough. After each trough has been filled with the blood serum of a particular patient diluted 2 to 3 with water or preferably with buffer B, apertures 18 are sealed off with plastic strips 26 and the jig is rotated for a time sufficient to insure adequate contact between the several blood serums and the several horizontal rows of islands.

E. After several hours rotation of the jig, the blood sera are removed from the troughs, the jig is separated and sheet 19 is thoroughly washed with a dilute solution of a protein such as albumin, preferably with a slightly alkaline buffered solution of albumin such as buffer B or buffer C. Buffer C is of the same composition as buffer B noted above, but contains in addition a small amount of about 1% by weight of a surface active agent, preferably a nonionic surfactant such as a polyglycol ether of an alkyl phenol or of a fatty alcohol, for example, polyoxyethylene sorbitan monolaurate sold by Atlas Chemical Company under the name "TWEEN-20" is a representative suitable compound. While this washing step is preferably performed with buffer C, adequate washing can, as noted above, be accomplished with a dilute solution of an albumin and distilled water.

The washing of the sheet in this step and also in step B is preferably done with the wash solutions described but the washing can be done with water if desired though a longer wash period would then be required for effective washing. F. After residual serums have been washed from the sheet 19, the sheet is immersed in a solution of the IGG fraction of an anti-immunoglobulin E(IgE) specific antiserum labeled with either a fluorescent material or a radioactive material. The IGG fraction of anti-immunoglobulin E specific antiserums from sheep, rabbits or goats are commercially available. The commercial serum fraction is desirably, but not necessarily, further purified, for instance, by an immunosorbent technique described by Robbins, Haimovich and Sela, Immunochemistry, Vol. 4, p. 11 (1967). In this purification, a bromacetyl cellulose-IgE conjugate is used.

The anti-IgE in the serum is bound to the IgE conjugate and after washing is eluted with a 0.2 molar glycine-HC1 buffer, pH 2.2 containing 0.1% human serum albumin.

Preparations of IgE suitable for conjugation to bromoacetylcellulose can be obtained from either IgE myeloma serum or from sera obtained from patients with high levels of IgE because of chronic parasitic infestation. The IgE can be fractionated by column chromatography using a method already described. (Ishizaka, K., Ishizaka, T., and Terry, W. D., J. Immunology 99: 849, 1967).

The purified anti-IgE preparation is preferably passed through a column of cellulose-albumin conjugated fibers to further reduce the nonspecific adherence of labeled impurities in the test. The anti-IgE material is labeled with either a fluorescent material such as fluorescein isothyocyanate, rhodamine or hydrazine hydrochloride salicylaldehyde. A variety of fluorescent materials may be used to label the IgE, the only restriction being that the fluorescent material should not itself directly react with cellulose. Alternatively, the anti-IgE may be labeled with a mildly radioactive material such as iodine 125 which can be added in the form of a sodium iodide solution. While iodine 125 is excellently adapted for labeling, the IgE serum, other radioactive materials having gamma energies in the range about 0.2 to 2 Mev, and half lives of 30 days or more (ease of storage) and which do not directly react with cellulose may be used. The labeling is accomplished by simply mixing the fluorescent material or the radioactive material with the anti-IgE. The method described by Coons (Int. Rev. Cytol) Vol. 5, p. 1 (1956) may be used to label the anti-IgE with a fluorescent material and the method described by Greenwood and Hunter (Nature), Vol. 194, p. 495 (1962), may be used to label the anti-IgE with iodine 125. The sheet 19 and the labeled anti-IgE are contacted for several hours at room temperature to permit reactions between the labeled anti-IgE and the patients' IgE contained on the sheet, if any. The sheet is then washed thoroughly with distilled water containing in solution a small amount of albumin or with buffer B or buffer C. The sheet is then analyzed to determine which of the islands have retained either fluorescent material or radioactive material, as the case may be.

Figure 6:
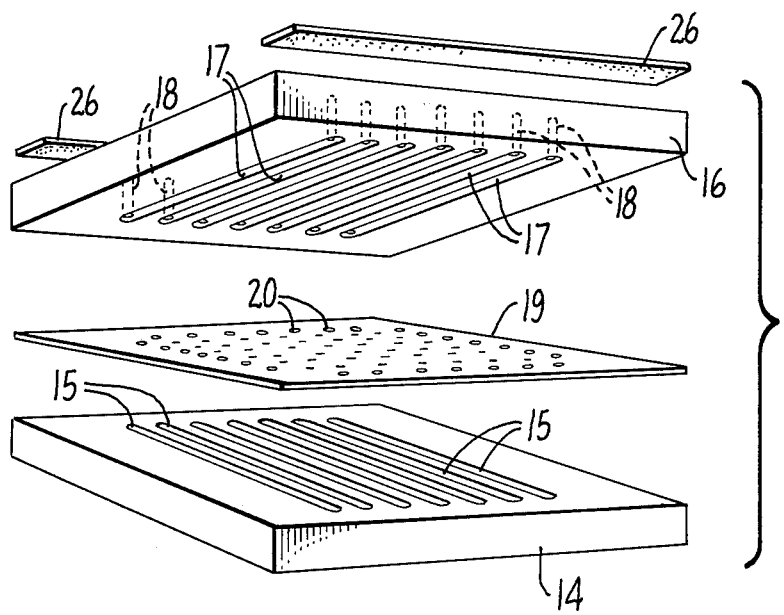
FIGS. 6–10 illustrate apparatus for making simultaneous determinations of hypersensitivity of a number of patients to a number of allergens.
Figure 7:
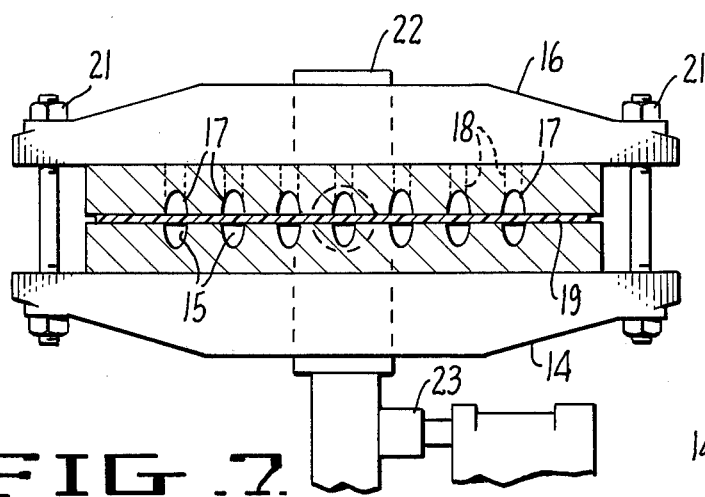
Figure 8:
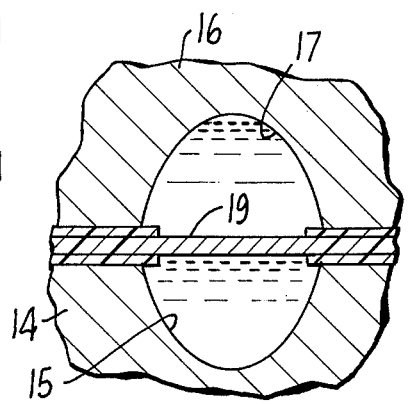

The jig shown in FIG. 6 is the preferred construction since it permits contacting both sides of the island areas on sheet 19 with allergen solutions or patients' sera as the case may be. The jig can be simplified and still remain effective by eliminating troughs 15 in bottom member 14 of the jig. Bottom member 14 would then be a flat surface on which sheet 19 is laid down so that the island rows will be in register with troughs 17 of top member 16 when the jig is assembled. With the jig so modified, only the upper surface of island areas 20 come into contact with the liquids employed in the test.

While the most practical arrangement of the islands on sheet 19 is such that they lie in straight rows, it is possible to arrange them so that they lay on parallel curved lines and to cut curved troughs in top and bottom member of the jig which would be in register with the curved lines of islands on the sheet.

$I^{125}$-labeled material can be quickly and efficiently identified by gamma-emission strip-scanning spectrometers which are commercially available and typically used for longitudinal scanning of paper electrophoresis strips.

More rapid determination of the test results can be obtained by recourse to an automatic scanning radiation spectrometer, or by a combination of autoradiography and a scanning desitomer. The latter has the disadvantage of an additional incubation, but has the decided advantage of less costly equipment and very rapid readout.

Autoradiographic readout of the sheet involves placing the sheet in contact with radiation-sensitive material for a period of time sufficient to allow appropriate radiation-induced changes take place. The radiation-sensitive material can be applied on a separate sheet, e.g. Kodak x-ray film no-screen, or applied to the allergen-containing sheet itself by dipping in a bath of photographic emulsion. In both cases the radiation-sensitive material is a light-sensitive film. It is also possible to use material which undergoes a change on exposure to gamma radiation. One example is gamma-sensitive, light-emitting phosphors, such as are now routinely used in diagnostic clinical radiography, to transduce gamma emission to the visible region where the light-sensitive film is particularly sensitive.

After the appropriate exposure period which may vary a few to several hours, the light sensitive material is treated to maximize and fix the changes which have occurred, e.g. film would be developed. The material is then scanned to detect and measure all islands where radiation-induced changes have taken place. These islands can be read and fed to a computer where the data is interpreted and printed for reporting to the interested parties.

Fluorescent labeled material can be read by exposing the entire strip to light of the exciting wavelength and simultaneously moving the sheet across a narrow slit behind which a photocell is situated which is sensitive to the wavelength of light emitted by the label. Alternately, the sheet can be placed before a photocell sensitive to the wavelength of emitted light and scanned by a laser whose light is of wavelength which is appropriate for excitation of the label.

When a particular island on the sheet is noted to be either fluorescent or radioactive, it is then known the patient who provided the serum is hypersensitive to that allergen which was contacted with that island of the sheet.

Sheets 19 are prepared by coating a paper sheet with a water repellant material so as to leave on the sheet a large number of uncoated islands so arranged that each island lies in a horizontal row of islands and also in a vertical row of islands and so arranged that the distances between each of the several horizontal rows are equal and the distances between each of the several vertical rows are equal. The spacing between horizontal rows and vertical rows may be made the same in which case a single jig may be used for allergen and sera impregnation of the island areas. Suitable water repellant materials include silicone grease or wax and paraffin wax but any water repellant material which adheres to paper may be used.

When, pursuant to the method described above, the allergens to which a patient is hypersensitive have been identified and the patient has been treated for the allergy by hyposensitization injections and it is desired to determine the efficacy of the therapy, the method above described can be modified to make such determination. To make this determination, an anti-immunoglobulin G (IgG) specific antiserum labeled either with a fluorescent material or a radioactive material is used in step F of the procedure instead of the anti-IgE specific antiserum. The anti-IgG will detect IgG type antibodies the presence of which will indicate effectiveness of the therapy applied. Determination that IgG type antibodies in the blood serum are increasing and that IgE type antibodies are simultaneously decreasing is a solid indication of therapy effectiveness.

Substitution of anti-IgG for anti-IgE in Step F can also be used to permit the determination of the degree of immunity of patients to organisms such as those of tetanus, diphtheria and rubella. In making these determinations, of course, extracts of these organisms are contacted with the sheet in step B instead of the allergen solutions used when hypersensitivity is being determined.

What is claimed is:

1. The method of simultaneously determining hypersensitivity of a number of human patients to a number of allergens which comprises providing a sheet of paper coated with a water impervious material so as to leave on the paper a large number of uncoated islands so arranged that each island lies in a horizontal row of islands and also in a vertical row of islands, enclosing the sheet in a jig having liquid receiving troughs in register with each horizontal row of islands, filling each trough with a separate identified allergen to impregnate the island areas with allergen, removing the allergens from the troughs and filling the troughs with an aqueous wash liquid to wash excess allergens from the paper, removing the wash liquid from the troughs and then removing the paper from the jig, enclosing the paper in a jig having liquid receiving troughs in register with the vertical rows of islands, filling each trough with diluted blood serum of a different human patient to contact the island areas with serum, removing the serums from the troughs, filling the troughs with an aqueous wash liquid to remove unreacted serum from the island areas, removing the wash liquid from the troughs and removing the paper from the jig, immersing the paper in a solution of anti-immunoglobulin E specific antiserum labeled with a cellulose inert fluorescent material or with a cellulose inert radioactive material and identifying the island areas which contain fluorescent or radioactive material.

2. The method of claim 1 in which the antiserum is labeled with a radioactive material and the sheet is placed in contact with a sheet of radiation sensitive material for a time sufficient to permit radioactive material contained on any island to cause radiation induced change of the radiation sensitive material.

3. The method of claim 2 wherein the radiation-sensitive material is an X-ray film.

4. A sheet of paper coated on both sides with a thin layer of an adherent hydrophobic material, the coating on the two sides being laid down so as to leave a plurality of uncoated islands on each side which are in register with the uncoated islands on the other side, the islands being so placed that they are in horizontal and vertical rows on the paper.

5. The sheets of paper defined in claim 4 wherein the center to center distances between adjacent islands in the vertical rows and in the horizontal rows are equal.

6. A jig for use in contacting island areas on a sheet of paper with liquid, comprising a generally rectangular top cover having a plurality of parallel troughs cut in its bottom surface and generally circular openings cut through the top surface to communicate with each end of each trough, a generally rectangular bottom member having a plurality of parallel troughs cut in its top surface and so arranged that the troughs in the bottom member and the troughs in the top cover are in register when the top cover is laid down on the bottom member and means for clamping the top cover and bottom member tightly together.

* * * * *